United States Patent [19]
Bates

[11] Patent Number: 4,561,844
[45] Date of Patent: Dec. 31, 1985

[54] ORTHODONTIC BRACKET

[76] Inventor: Lyn V. Bates, 3701 Market Ave. N., Canton, Ohio 44714

[21] Appl. No.: 659,091

[22] Filed: Oct. 9, 1984

[51] Int. Cl.⁴ .............................................. A61C 3/00
[52] U.S. Cl. ..................................... 433/14; 433/13; 433/16; 433/10
[58] Field of Search .................. 433/14, 13, 10, 8, 16, 433/9, 15

[56] References Cited

U.S. PATENT DOCUMENTS

| | | | |
|---|---|---|---|
| 1,280,628 | 10/1918 | Angle | 433/14 |
| 1,821,717 | 9/1931 | Atkinson | 433/14 |
| 2,671,964 | 3/1954 | Russell et al. | 433/13 |
| 2,908,974 | 10/1959 | Stifter | 433/16 |
| 3,128,553 | 4/1964 | Begg | 433/14 |
| 3,435,527 | 4/1969 | Kesling | 433/14 |
| 3,660,900 | 5/1972 | Andrews | 433/16 |
| 4,171,568 | 10/1979 | Forster | 433/10 |
| 4,249,897 | 2/1981 | Anderson | 433/16 |
| 4,268,249 | 5/1981 | Forster | 433/10 |
| 4,443,189 | 4/1984 | Wildman | 433/13 |

Primary Examiner—John J. Wilson
Attorney, Agent, or Firm—Michael Sand Co.

[57] ABSTRACT

An improved orthodontic bracket for mounting on the inside surface or lingual of a tooth having an upwardly opening longitudinal channel for receiving an arch wire therein. The bracket includes a one-piece body having a locking groove formed in a front wall. A locking pin is rotatably mounted in a key-hole shaped opening formed in the body and is removable therefrom for replacement if it becomes damaged. The locking pin has a locking plate at one end of a shaft which is engageable in the locking groove of the body wall to secure an arch wire in the channel. A locking tab is mounted on the other end of the shaft and moves along a ramped surface formed in a recess for securing the locking plate in the locking groove. Rotation of the locking pin 180° moves the locking plate between an arch wire retaining or locked position and an arch wire receiving or unlocked position. Rotation of the pin 90° from either position will align the locking tab with the key-shaped opening enabling complete removal of the locking pin from the bracket body. A wedge block also may be mounted between the bracket body and inside surface of the tooth to change the mounting angle of the arch wire to obtain various force components on the tooth to move the tooth in various desired directions.

20 Claims, 21 Drawing Figures

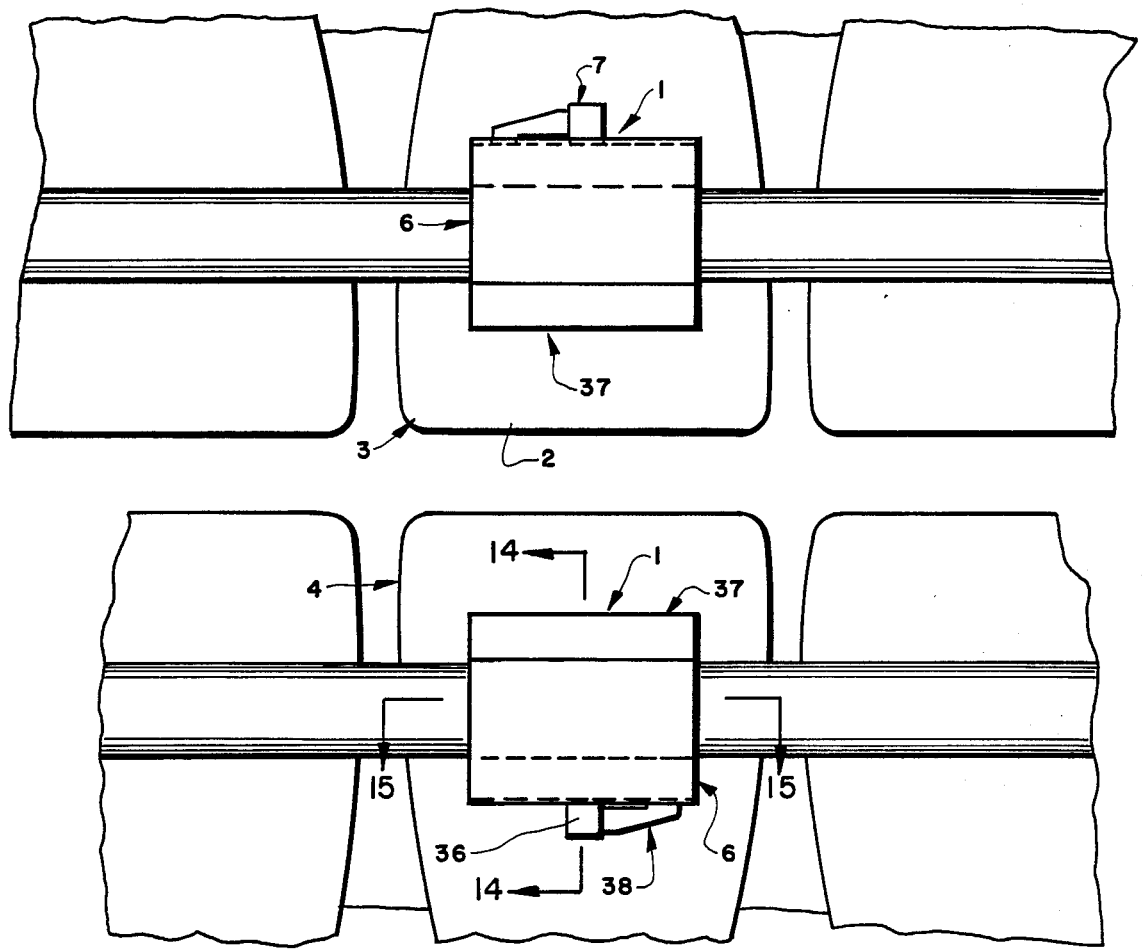
FIG. 1
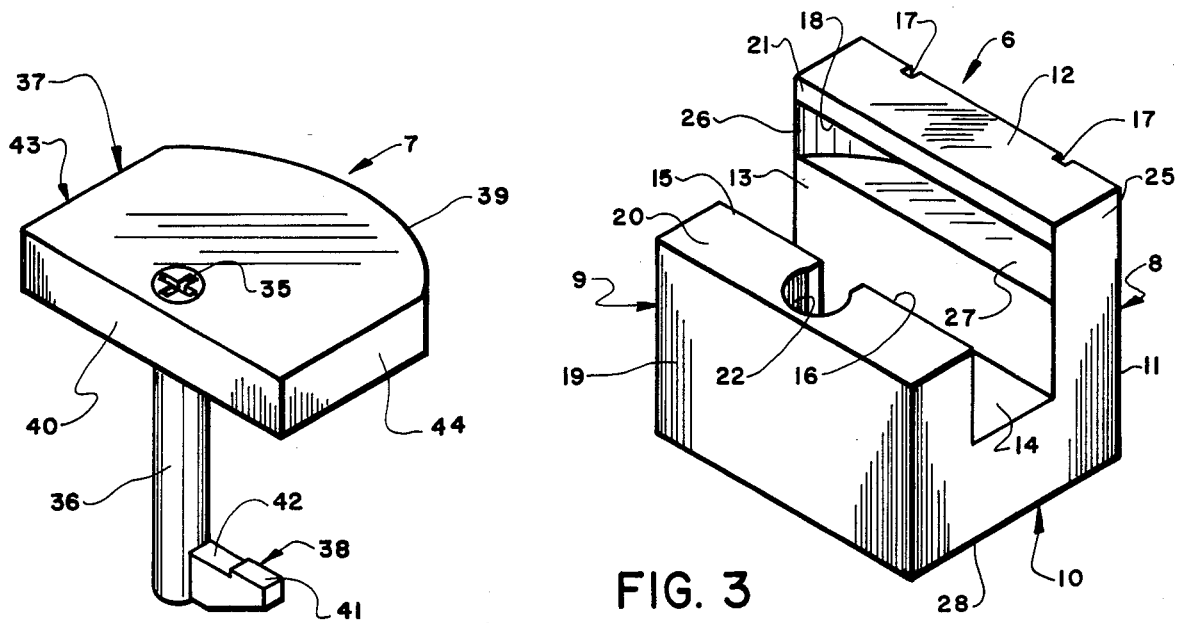
FIG. 2
FIG. 3

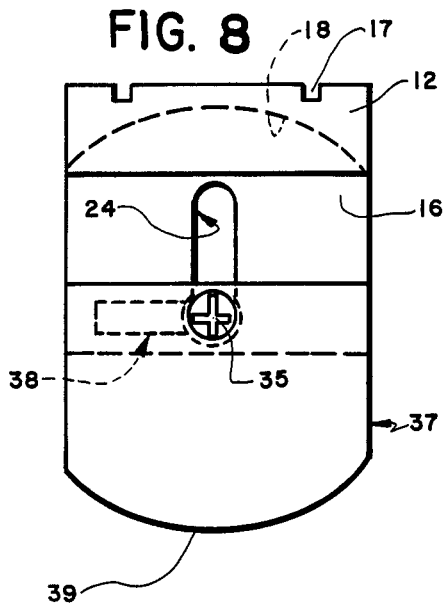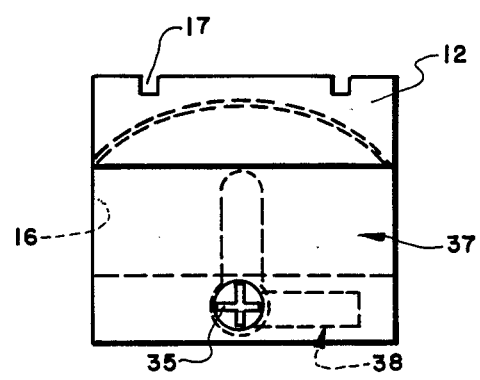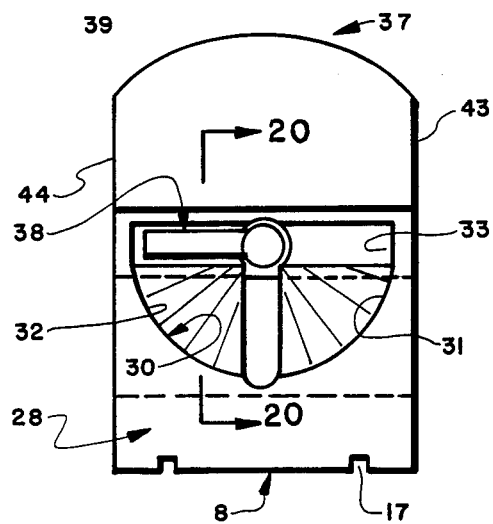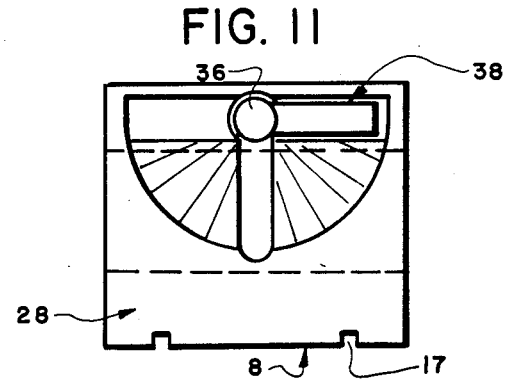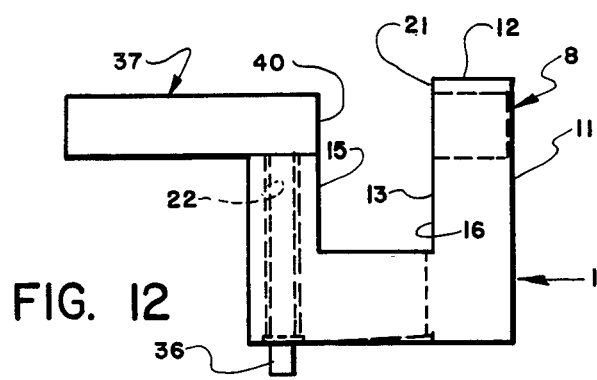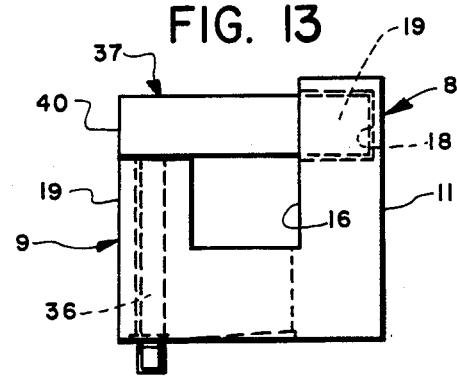

ORTHODONTIC BRACKET

TECHNICAL FIELD

The invention relates to orthodontic brackets and in particular to a bracket mounted on the tooth lingual for receiving and securely retaining an arch wire in a vertical groove formed in the bracket.

BACKGROUND ART

Various types of orthodontic brackets and appliances have been devised for mounting on a patient's teeth for relocating one or more teeth in the patient's mouth. Heretofore, such brackets were placed on the outer surface of the teeth and provided a very unsightly appearance to the patient. It also caused considerable discomfort due to the rubbing of the inside of the patient's lips against the protruding brackets. Recently, attempts have been made to mount the brackets on the rear surface or tooth lingual to eliminate the bracket from being exposed eliminating one of the main objectives to wearing such brackets or orthodontic appliances, namely the unsightly appearance. Also, mounting of the bracket on the tooth lingual eliminates the uncomfortable contact with the inside surface of the patient's lips.

However, the mounting of the brackets on the inside surface of the teeth increases the difficulty of the installation of arch wires and their subsequent attachment to the brackets due to the reduced work area and in accessability by the dentist. During the course of treatment of a patient, the arch wire is replaced many times in order to achieve the desired teeth movement. Such arch wire replacement consumes considerable time by the dentist and increases the discomfort of the patient.

Previous orthodontic brackets were formed with a horizontal channel or slot into which the arch wire was inserted and secured by tie wires or the like. The use of such horizontally opening bracket channels is unsatisfactory when the bracket is mounted on the inside surface of the tooth. Some prior brackets have been provided with a vertically accessable top opening channel for insertion and removal of the arch wire. Examples of such constructions are shown in U.S. Pat. Nos. 1,280,628; 1,821,171; and 3,435,527. However, most of these brackets are intended for use on the exterior surface of the tooth.

The construction of U.S. Pat. No. 4,171,568 is believed to be the closest prior art to my invention since it shows the use of a locking element for maintaining the arch wire in a secured position within a channel formed in the bracket. However, the channel is a horizontally opening channel designed for use on the labial (outside the tooth surface) and not a vertical opening channel which greatly facilitates the installation and removal of the arch wire on the lingual. Also, the locking pin of this prior bracket construction is not removable and should it become damaged during its period of use it would require replacement of the entire bracket which is time consuming and especially difficult on the linqual for the dentist and discomforting for the patient.

The bracket construction of U.S. Pat. No. 4,268,249 discloses a top opening vertical channel for receiving an arch wire in combination with a locking element. However, the bracket of this patent requires a separate insert which forms the base of the channel and requires a special tool for locking the arch wire retainer in position. Also, the locking retainer is not replaceable should it become damaged which would require replacement of the entire bracket. Also, an individual orthodontis could not fabricate a rectangular torquing arch wire in his office because of the extreme torque angle of the slot when used on the lingual.

Accordingly, the need has existed for an improved orthodontic bracket which has a vertically opening channel for receivably mounting an arch wire therein together with removable locking means for securing the arch wire in position.

DISCLOURE OF THE INVENTION

Objectives of the invention include providing an improved orthodontic bracket adapted to be mounted on the tooth lingual which is provided with a vertically opening slot or channel enabling an arch wire to be dropped into the slot and secured therein by a removably mounted locking mechanism. Another objective is to provide such a bracket which is formed by two separate components, a generally U-shaped body which is adapted to be secured to the tooth lingual by an adhesive or the like and a removably mounted locking pin in which the locking pin has a locking plate that is trapped within a groove formed in the bracket body to securely retain the arch wire in the vertically opening channel and which resist vertical movement of the arch wire by the entrapping of the locking pin within the bracket body; and in which the locking pin has tab means engagement in a recess formed in a ramped area of the bracket body for securing the locking pin in both a locked arch wire retaining position and in an alternate fully opened position for receiving the arch wire.

A still further objective of the invention is to provide such a bracket which increases the speed of installation of the arch wires and reduces parts from "floating" around the patient's mouth which can be harmful to the patient, such as loose ends of cut ligatures, and which eliminates any loose pieces that could possibly remain in the patient's mouth after replacing the arch wire. Another objective is to provide such an improved bracket construction in which the mounting face of the bracket body can be formed at various angles enabling torque to be built into the bracket whereby the torque generated by the arch wire is directed in a predetermined direction against the tooth for moving the tooth in the desired direction; in which an insert may be used for varying the size of the arch wire receiving slot or channel; and in which the insert may be provided with attaching hooks for securing auxiliary wires or elastics thereto.

A further objective is to provide such an improved orthodontic bracket in which the bracket body and locking pin may be formed of stainless steel or plastic or a combination of both which provides sanitary dental applicance, and in which the bracket is mounted on the rear surface of the tooth so as not to be visible when installed on the patient thereby improving the patient's appearnce and reducing resistance to wearing such orthodontic appliances. Also wedge blocks may be provided in differing angles for attachment to the bracket to enable customizing bracket torque for each tooth.

These objectives and advantages are obtained by the improved orthodontic bracket of the invention, the general nature of which may be stated as including a one-piece generally U-shaped bracket body have a front wall adapted to be secured to the tooth linqual, an end wall and an outer wall spaced from the front wall forming a vertical arch wire receiving channel therebetween; a groove formed in the front wall spaced from the end wall and communicating with the channel; a vertically extending hole formed in and extending completely through the outer wall; a locking pin having a shaft rotatably mounted in the outer wall hole, a locking plate mounted on one end of the shaft and removably engageable in the front wall groove for locking an arch wire in the channel, and a tab mounted on the other end of the shaft for releasably securing the locking plate in the front wall groove engaged position; and a slot formed in the end wall of the bracket body and communicating with the shaft receiving outer wall hole, said slot being complementary to the tab means permitting the locking pin to be removed from the bracket body.

BRIEF DESCRIPTION OF THE DRAWINGS

A preferred embodiment of the invention, illustrative of the best mode in which applicant contemplates applying the principles, is set forth in the following description and is shown in the drawings and is particularly and distinctly pointed out and set forth in the appended claims.

FIG. 1 is a diagrammatic fragmentary perspective view showing the improved orthodontic bracket of the invention mounted on the inside surface or lingual of both an upper and lower tooth;

FIG. 2 is an enlarged perspective view of the locking pin components of the improved bracket construction;

FIG. 3 is an enlarged perspective view of the main body portion of the improved bracket with which the locking pin of FIG. 2 is incorporated;

FIG. 8 is a top plan view of the improved bracket with the locking pin shown in an open arch wire receiving position;

FIG. 9 is a top plan view similar to FIG. 8 with the locking pin being shown in closed arch wire receiving position;

FIG. 10 is a bottom plan view of the bracket body of FIG. 8 with the locking pin in an open arch wire receiving position;

FIG. 11 is a bottom plan view of the improved bracket of FIG. 9 with the locking pin shown in closed position;

FIG. 12 is a right hand elevational view of the bracket of FIG. 8 with the locking pin in open position;

FIG. 13 is a right hand end elevational view of the bracket of FIG. 9 with the locking pin shown in closed position;

Similar numerals refer to similar parts throughout the drawings.

BEST MODE FOR CARRYING OUT THE INVENTION

Figure 21:
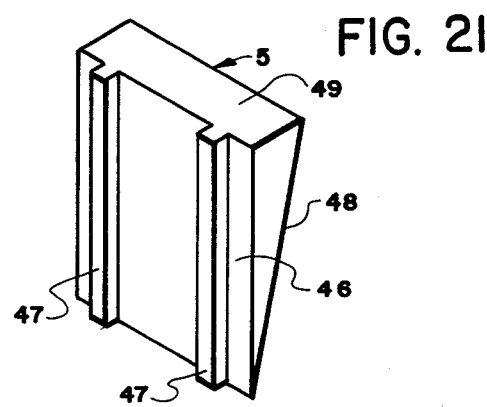
FIG. 21 is a perspective view of the wedge block.

The improved orthodontic bracket is indicated generally at 1, and is shown in FIG. 1 mounted on the inside surface or tooth lingual 2 on both an upper and lower tooth, indicated at 3 and 4. Bracket 1 includes two main components, a one-piece generally U-shaped bracket body indicated generally at 6 (FIG. 3), and a locking pin indicated generally at 7 (FIG. 2). A wedge block indicated generally at 5, is shown in FIG. 21 and may be used with bracket 1 for certain patients as described more fully below.

Figure 14:
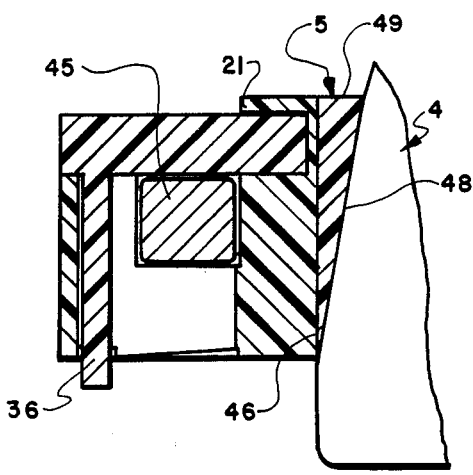
FIG. 14 is an enlarged fragmentary sectional view taken on line 14—14, FIG. 1; with a wedge block being shown mounted between the bracket and the tooth.
Figure 15:
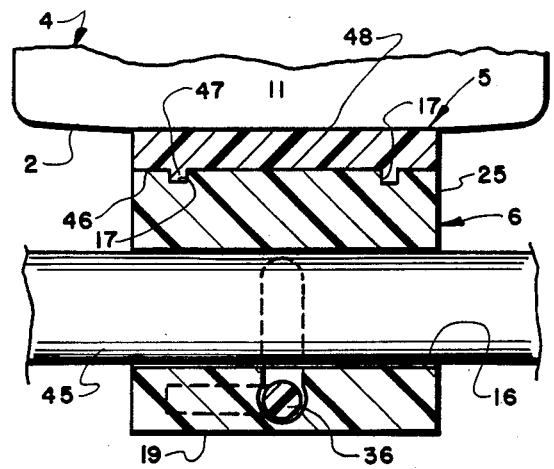
FIG. 15 is an enlarged fragmentary sectional view taken on line 15—15, FIG. 1.

Bracket body 6 is an integral one-piece member preferably formed of stainless steel or plastic. Body 6 includes a front wall indicated generally at 8 which is formed with a pair of spaced parallel slots or kerfs 17 for removably mounting wedge block 5 thereon. Body 6 further includes an outer wall indicated generally at 9, which is spaced from and generally parallel to front wall 8 and a connecting end wall indicated generally at 10. Front wall 8 preferably has a generally rectangular shape with a front surface 11, a top surface 12, and an inner channel forming surface 13. Front surface 11 is adapted to be placed against the tooth lingual 2 and secured thereon by an adhesive or other known type of attachment means unless wedge block 5 is mounted therebetween as shown in FIGS. 14 and 15. Top surface 12 of front wall 8 preferably is flat and extends in a generally horizontal direction when body 6 is mounted on a tooth and inside surface 13 may extend parallel with front surface 11 as shown in FIGS. 3 and 12. Inside surface 13 together with end wall inner surface 14 and the interior surface 15 of outer wall 9 form a U-shaped arch wire receiving channel 16 therebetween. Channel 16 is a vertical longitudinal extending channel having an open top or bottom depending upon which tooth lingual it is mounted on as shown in FIG. 1, and has a rectangular cross-sectional configuration as shown particularly in FIGS. 12 and 13.

Front surface 11 of front wall 8 may extend at an angle with respect to inside surface 13 instead of parallel as shown in the drawings in order to mount bracket body 6 at an angle on the tooth lingual whereby the pressure exerted by an arch wire mounted within channel 16 exerts a predetermined directional force component on the tooth to move the tooth in the desired direction. Thus, by changing the mounting angle of bracket body 6 on the inside tooth surface, different force components can be exerted on the tooth to assist in moving the tooth in various directions with respect to the adjacent teeth. This same result also is achieved by the use of wedge block 5 as described below.

Figure 4:
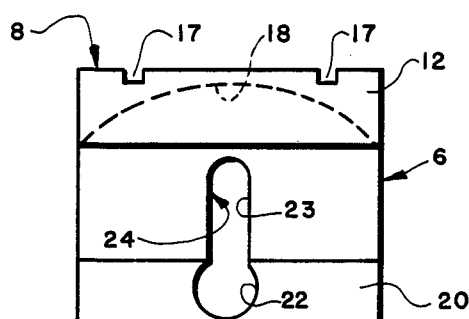
FIG. 4 is a top plan view of the improved bracket body of FIG. 3 with the locking pin removed therefrom.

In accordance with one of the features of the invention, an arcuate shaped concave groove 18 is formed in surface 13 of end wall 8. Groove 18 preferably has a semicircular configuration and is formed below top surface 12 to provide a ledge or wall 21 above the groove for trapping a locking plate therein as described more fully below. Arcuate shaped groove 18 preferably extends throughout the longitudinal length of front wall 8 between side walls 25 and 26. Also, top surface 20 of outer wall 9 lies in a common horizontal plane as bottom surface 27 of groove 18 as shown particularly in FIGS. 12 and 13. Outer wall 9 includes an outer surface 19 which is generally parallel with channel forming inside surface 15. A vertically extending, generally semicircular hole 22 is formed vertically through end wall 9 and bottom wall 10 and communicates with an elonated slot 23 formed in end wall 10. Hole 22 and slot 23 together form a locking pin removal opening indicated generally at 24 (FIGS. 4 and 6).

Figure 6:
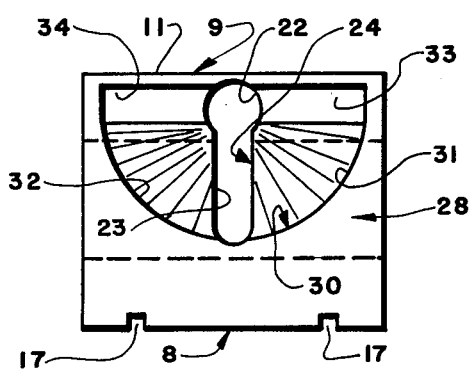
FIG. 6 is a bottom plan view of the bracket body of FIGS. 3 through 5.

Outer surface 28 of body 6 preferably is flat having a rectangular configuration and is formed by the integrally joined portions of walls 8, 9, and 10 and is shown particularly in FIG. 6. In accordance with another of the main features of the invention, a semicircular shaped recess 30 is formed in bottom surface 28 with opening 24 being located in the center thereof and extending in a radial direction from adjacent outer wall 9 toward front wall 8. Opening 24 divides recess 30 into a pair of quadrant shaped recesses 31 and 32 each having ramped surfaces inclined upwardly from opening 24 toward outer surface 19 of rear wall 9. Ramp surfaces 31 and 32 terminate in a pair of longitudinally aligned end depressions 33 and 34, respectively (FIGS. 6 and 20) extending inwardly from the raised end edges of the ramp surfaces.

Locking pin 7 includes a cylindrical shaft 36 having a locking plate 37 mounted on one end thereof and a locking tab 38 mounted on the opposite end. Locking plate 37 is generally flat having a rectangular configuration with a curved outer end 39 which is complementary to groove 18 of body 6 and is slidably received therein when locking pin 7 is in a locked or arch wire receiving position as shown particularly in FIG. 13. A tool receiving opening 35 (FIG. 2) is formed in plate 37 in axial alignment with shaft 36 for receiving the end of a tool for rotating locking pin 7 between the arch wire receiving and retaining positions.

Shaft 36 is connected to plate 37 adjacent its outer edge 40 so as to provide an eccentric movement to plate 37 upon rotation of shaft 36 within hole 22 of the bracket body. Locking tab 38 extends radially outwardly from shaft 36 and is provided with a locking nub 41 projecting upwardly from a flat surface 42. The longitudinal length of plate 37 defined by straight side surfaces 43 and 44 is equal to the longitudinal length of top surface 20 of outer wall 9 of body 6.

Locking pin 7 is pivotally mounted on body 6 for movement between a locked or arch wire retaining position as shown in FIG. 13, and an open arch wire receiving position as shown in FIG. 12. Shaft 36 is telescopically rotatably mounted within bracket body hole 22 with locking nub 41 of tab 38 being engageable with ramp surfaces of recesses 31 and 32. When in the arch wire retaining position of FIG. 13, rear surface 40 of plate 37 aligns with surface 19 of outer wall 9, and when in the arch wire receiving position of FIG. 12, it vertically aligns with inside surface 15 of outer wall 9. This provides a bracket which is relatively free of protruding parts that would be uncomfortable to a patient. Also, this mounting arrangement of plate 37 provides a completely opened vertical channel 16 as shown in FIG. 12 for receiving an arch wire therein. When in the locked position of FIG. 13, outer curved end 39 of locking plate 37 is received within front wall groove 18 and is prevented from any vertical movement by the retaining ledge 21 formed above groove 18. As shown in FIG. 13 when in the closed position, locking plate 37 forms a longitudinally extending rectangular-shaped in cross section channel 16 complementary to a usual rectangular arch wire 45 as shown in FIGS. 14 and 15.

In the preferred embodiment, arch wire receiving channel 16 will have a depth of 0.022 inches and a width of 0.028 inches which is complementary with the size of a usual arch wire of the type to be attached to the teeth by improved bracket 1. These dimensions provide for a snug fit between the bracket body and arch wire and with locking plate 37 of locking pin 7 when in the closed position.

The operation of improved bracket 1 is easily seen by a review of the various figures and in particular FIGS. 12 and 13. After attaching one or more brackets to the tooth lingual, locking pin 7 is rotated to the open position as shown in FIG. 12. Arch wire 45 is either inserted vertically from above or vertically from below into channel 16 depending upon whether the bracket is attached to an upper or lower tooth as shown in FIG. 1. Locking pin 7 then is rotated 180° to the locked position of FIG. 13. When approaching locked position of FIG. 13, locking nub 41 will move upwardly along the ramp surface of recess 31 until reaching depression 33 after which it will drop into the depression and be trapped therein upon locking plate 37 reaching its fully latched position. The engagement of locking nub 41 in depression 33 will secure the locking pin in the locked position preventing premature movement of the locking pin. Also, ledge 21 of front wall 8 secures curved outer edge 39 of locking plate 37 in groove 18 preventing any vertical movement of the locking pin by forces exerted thereon by the arch wire.

Figure 20:
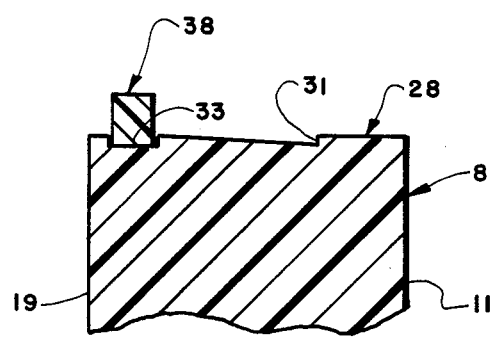
FIG. 20 is a fragmentary sectional view taken on lines 20—20, FIG. 10.
Figure 5:
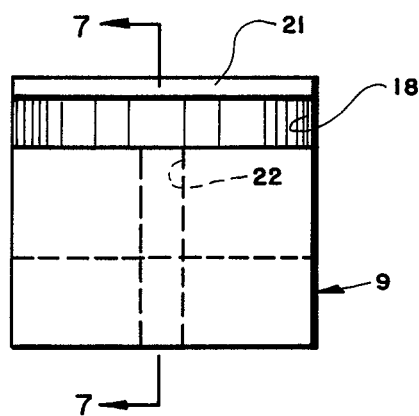
FIG. 5 is a front elevational view of the improved locking bracket body of FIGS. 3 and 4.
Figure 7:
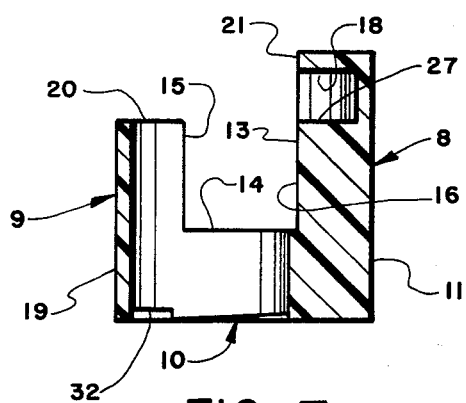
FIG. 7 is a sectional view taken on line 7—7, FIG. 5.

Prior to moving locking pin 7 to its locked position it will be in the position shown in FIGS. 8 and 10 in which locking nub 41 is located in depression 34 as shown in FIG. 20 maintaining locking pin 7 in its fully opened position of FIG. 12 facilitating the placement of the arch wire in channel 16. This arrangement provides for a positive retention of the locking pin in the open position until manually moved by the dentist to the closed position. This facilitates the placement and removal of the arch wire into and from channel 16.

Figure 16:
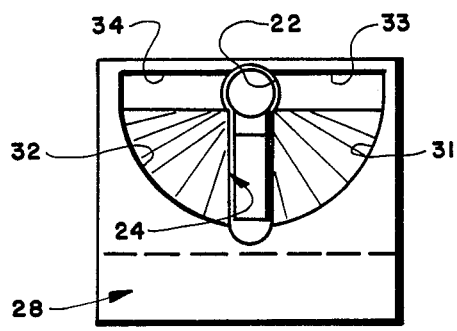
FIG. 16 is a bottom plan view of the improved bracket similar to FIGS. 10 and 11 with the locking pin shown in an intermediate position enabling the locking pin to be removed from the bracket body.

In accordance with one of the main features of the invention, should locking pin 7 become damaged and require placement, the same is easily accomplished by rotating the locking pin 90° from either the locked or unlocked position. This movement will align locking tab 38 with opening 24 as shown in FIG. 16 which will enable the locking pin to be removed vertically from its engagement with bracket body 6. A new locking pin 7 then is reinstalled in existing body 6 by the same procedure. Locking pin 7 thus can be replaced without disturbing the mounting of bracket body 6 on the tooth lingual which heretofore was a problem since the entire bracket body had to be removed from the tooth surface and a new bracket attached.

Wedge block 5 referred to above is a solid wedge-shaped member as shown in FIG. 21, and preferably is formed of the same material, such as stainless steel or plastic, as is bracket body 6. Wedge block 5 includes a vertically extending wall 46 on which a pair of spaced parallel ribs 47 are formed which are received within wedge block kerfs 17 as shown in FIGS. 14 and 15. Wedge block 5 further includes an inclined surface 48 which abuts against the tooth surface when mounting bracket body 6 on a tooth. Surfaces 46 and 48 terminate at one end in an apex and at the opposite end in a connecting flat surface 49.

Wedge block 5 is an optional feature which may or may not be used with bracket body 6 depending upon the discretion of the dentist and the particular result to be achieved by the orthodontic bracket. Instead of forming front wall 8 of bracket body 6 at a predetermined angle for placement against the tooth surface to achieve various force components against the tooth, the shape of the bracket body including the front wall 8, will remain constant and by mounting various sloped wedge blocks 5 between the bracket body and tooth surface, various directional torques and forces may be exerted on the tooth. Wedge block 5 is easily inserted within kerfs 17 and secured therein by a spot weld, an adhesive, or the like. Inclined surface 48 then is secured against the tooth lingual as shown in FIGS. 14 and 15 by usual bracket attachment means.

Wedge block 5 will enable a dentist to maintain a relatively small inventory of bracket bodies 6 of the same general shape and configuration, while permitting different torques and directional forces to be exerted against the tooth by varying the angle of inclination of sloped surface 48 with respect to surface 46 of wedge block 5. Thus, a relatively large supply of various angled wedge blocks 5 may be maintained in inventory at a considerable reduced cost to the dentist than that required to keep a similar number of bracket bodies having different inclined front surfaces.

Bracket 1 may be used with or without a wedge block 5, with block 5 being a modification thereto that will provide desirable results at a reduced cost. Preferably wedge block kerfs 17 will not be formed in front wall 8 of body 6 if the body is mounted directly on the tooth. However, these kerfs can be filled with various substances even if wall 8 having kerfs 17 formed therein is placed directly against the inside surface of the tooth.

Wedge block 5 enables the dentist to adjust the individual variations in the tooth anatomy and provide that the top edge of the rectangular arch wire will be parallel with the chewing plane of the teeth when they are all properly aligned. Some teeth need a greater angulation than others and if extractions are required in the treatment plan the front teeth require more torque.

Figure 17:
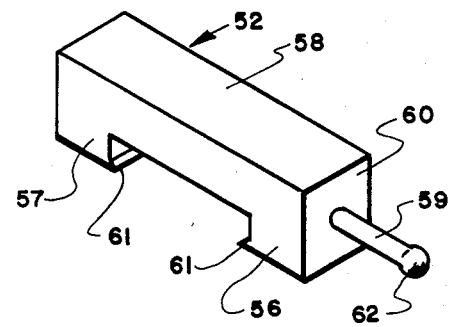
FIG. 17 is a perspective view of an insert which may be used in conjunction with a modified bracket assembly shown particularly in FIG. 18.
Figure 19:
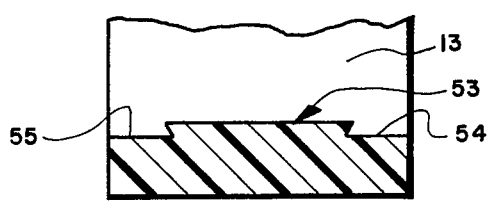
FIG. 19 is a fragmentary sectional view on line 19—19, FIG. 18.
Figure 18:
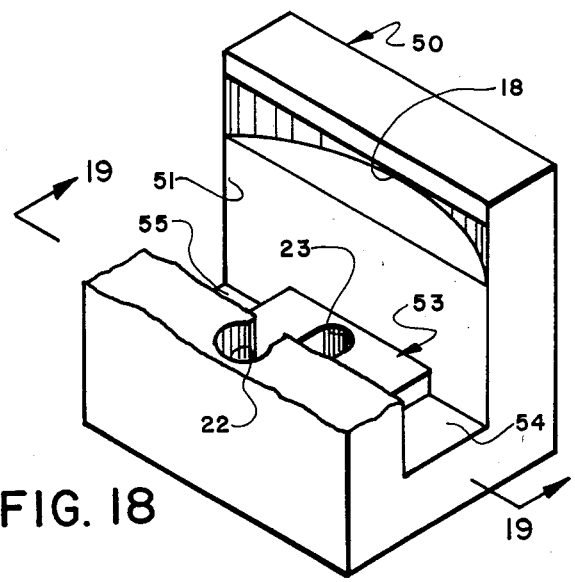
FIG. 18 is a perspective view with portions broken away showing a modified bracket body construction.

A modified form of the improved bracket is indicated generally at 50 and is shown particularly in FIGS. 17-19. Modified bracket 50 is similar in most respects to bracket 1 except that the arch wire receiving channel which is indicated at 51, has a greater depth than channel 16 of bracket 1 enabling it to receive an insert, indicated generally at 52 (FIG. 17). Bracket 50 is formed with the same key-hole shaped opening 24 as is bracket 1 and with the same arcuate shaped locking plate groove 18. The channel forming lower wall 53 in which pin receiving hole 22 is formed, is provided with a pair of end cutouts 54 and 55 for receiving rectangular projections 56 and 57 of insert 52 to prevent longitudinal movement of the insert after being placed in channel 51.

Insert 52 is a generally rectangular shaped block formed of stainless steel or plastic having a flat top surface 58 and outwardly projecting legs 56 and 57. In accordance with one of the main features of bracket 50, a pin 59 or similar attachment device is attached to or embedded in and projects outwardly from side surface 60. Pin 59 provides a readily available means of attaching resilient bands or clips extending from other portions of the orthodontic appliances. The outer end 62 of pin 59 is rounded to protect the patient's mouth and tongue.

Preferably a pair of small nubs 61 extend along the inner surface of legs 56 and 57 to provide a "snap-in" feature when the insert is placed within channel 51 in cooperation with the central portion of bottom wall 53. An arch wire 45 rests upon top surface 58 of insert 52 when inserted within channel 51. The longitudinal length of insert 52 is complementary to that of bracket 50 so that the side surfaces of the insert correspond to the side surfaces of the bracket body when placed therein eliminating as many projections as possible for the patient's comfort.

Modified bracket 50 also may be provided with wedge block receiving kerfs in the front wall for mounting a wedge block 5 thereon in a similar manner as described above for bracket 1.

The main advantage achieved by insert 52 is that it provides an attachment point for other tie wires, bands, etc. without affecting the depth and size of the arch wire receiving channel and the locking feature achieved by removable locking pin 7. Another advantage of inserts 52 is that by varying the thickness thereof the depth of the arch wire receiving channel can be adjusted for receiving various sizes of arch wires in contrast to bracket 1 which has a fixed depth. The width of channel 51 also may have a different width than that of channel 16 in order to accomodate other sizes and arch wire configurations.

Although the usual width of channel 16 for bracket 1 was indicated as having a width of 0.028 inches and a depth of 0.022 inches another commonly used sized arch wire would have a width of 0.025 inches and a depth of 0.018 inches. Channel 51 of bracket 50 as well as channel 16 of bracket 1 may be sized for this other common size of arch wire.

Accordingly, improved brackets 1 and 50 provide an orthodontal appliance which is adapted to be placed on the tooth lingual by usual attachment means for receiving an arch wire in a rectangular shaped lonqitudinally extending channel which receives the arch wire in a vertical direction, either from above or below depending upon whether the bracket is mounted on an upper or lower tooth, and which has a locking pin which securely clamps the arch wire in position, and which can be removed easily for replacement should it become damaged during its relatively long period of use within a patient's mouth. Also, the bracket body and locking pin may be formed entirely of stainless steel or plastic or a combination of both. In the preferred embodiment, it is believed that the main bracket body will be formed of stainless steel and the locking pin formed of plastic. The formation of locking pin 7 of plastic or similar synthetic material assists the locking nub 41 to lock the pin in its fully opened and fully closed positions as described above. Also, the formation of insert 52 of a plastic material together with locking nubs 61 provides sufficient resiliency for locking the insert in position within cutouts 54 and 55.

Accordingly, the improved orthodontic bracket is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness, and understanding; but no unnecessary limitations are to be implied therefrom beyond the requirements of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the improved orthodontic bracket is constructed and used, the characteristics of the construction, and the advantageous, new and useful results obtained; the new and useful structures, devices, elements, arrangements, parts, and combinations, are set forth in the appended claims.

What is claimed is:

1. An orthodontic bracket for mounting on the inside surface or lingual of a tooth for retaining an arch wire including:
   (a) a one-piece generally U-shaped bracket body having a front wall adapted to be secured to the tooth lingual, an end wall and an outer wall spaced from the front wall forming a vertical arch wire receiving channel therebetween;
   (b) a groove formed in the front wall spaced from the end wall and communicating with the channel;
   (c) a vertically extending hole formed in and extending completely through the outer wall;
   (d) a locking pin having a shaft rotatably mounted in the outer wall hole, a locking plate mounted on one end of the shaft and removably engageable in the front wall groove for locking an arch wire in the channel, and a tab mounted on the other end of the shaft for releaseably securing the locking plate in the front wall groove engaged position;
   (e) a slot formed in the end wall of the bracket body and communicating with the shaft receiving outer wall hole, said slot being complementary to the tab means permitting the locking pin to be removed from the bracket body.

2. The orthodontic bracket defined in claim 1 in which a semicircular recess is formed in an outer surface of the end wall and communicates with the slot and the outer wall hole; and in which the recess has a ramped surface which is engaged by the locking pin tab to assist in maintaining the locking plate in an arch wire retaining position in the front wall groove.

3. The orthodontic bracket defined in claim 2 in which the slot and outer wall hole forms a generally key-hole shaped opening which is located in the center portion of the end wall recess.

4. The orthodontic bracket defined in claim 3 in which the locking pin aligns with the key-shaped opening for removing the locking pin from the bracket body upon rotation of the locking pin 90° from the arch wire retaining position.

5. The orthodontic bracket defined in claim 4 in which the locking pin shaft is cylindrical with the locking tab extending radially outwardly therefrom with a width less than the diameter of the shaft.

6. The orthodontic bracket defined in claim 2 in which a depression is formed in the end wall recess for receiving a nub formed on the locking pin tab to retain the locking pin in the arch wire retaining position.

7. The orthodontic bracket defined in claim 4 in which a second depression is formed in the end wall recess at an upper end of the ramped surface to retain the locking plate in an arch wire receiving position upon rotation of the locking pin approximately 180° from the outer arch wire retaining position.

8. The orthodontic bracket defined in claim 1 in which the locking plate includes a curved front edge which is engageable in the front wall groove and a back edge which aligns with an outer surface of the outer wall when the locking plate is in the arch wire retaining position, and which aligns the inner or channel forming surface of the outer wall when the locking plate is in an arch wire receiving position.

9. The orthodontic bracket defined in claim 1 in which the channel has a rectangular cross sectional configuration in which the width is greater than the depth.

10. The orthodontic bracket defined in claim 9 in which the depth of the channel is 0.022 inches and the width is 0.028 inches.

11. The orthodontic bracket defined in claim 9 in which the depth of the channel is 0.018 inches and the width is 0.025 inches.

12. The orthodontic bracket defined in claim 9 in which insert means is removably mounted in the channel for adjusting the depth of said channel.

13. The orthodontic bracket defined in claim 12 in which the insert means includes attachment means formed thereon for securing a tie wire thereto from another bracket.

14. The orthodontic bracket defined in claim 12 in which recess means is formed in the end wall of the bracket body for receiving the insert means therein.

15. The orthodontic bracket defined in claim 14 in which the insert means includes a pair of spaced rectangular projections; and in which said insert means projections are received in the recess means for maintaining the insert means in longitudinal alignment within the bracket channel.

16. The orthodontic bracket defined in claim 12 in which the insert means has a generally U-shaped configuration.

17. The orthodontic bracket defined in claim 1 in which wedge means is mounted on the front wall of the bracket body for changing the mounting angle of the bracket body with respect to the tooth when mounted on the tooth lingual.

18. The orthodontic bracket defined in claim 17 in which kerf means is formed in the front wall of the bracket body for mounting the wedge means thereon.

19. The orthodontic bracket defined in claim 18 in which the kerf means includes a pair of spaced parallel kerfs extending vertically along the front wall of the bracket body; and in which the wedge means includes a wedge-shaped member having a pair of spaced parallel ribs formed on a surface thereof, with said ribs being engaged in the kerfs for mounting the wedge member on the front wall of the bracket body.

20. The orthodontic bracket defined in claim 1 in which means is formed on the locking plate for engagement by a tool for rotating the locking plate between an arch wire retaining position and an arch wire receiving position.

* * * * *